(12) United States Patent
Chakradhar

(10) Patent No.: US 8,631,686 B2
(45) Date of Patent: Jan. 21, 2014

(54) SYSTEM TO MEASURE THE ABSORPTIVE CAPABILITIES OF POROUS MATERIALS USED IN OIL SPILL REMEDIATION

(76) Inventor: Vineel Chakradhar, Lincroft, NJ (US)

(*) Notice: Subject to any disclaimer, the term of this patent is extended or adjusted under 35 U.S.C. 154(b) by 275 days.

(21) Appl. No.: 13/274,528

(22) Filed: Oct. 17, 2011

(65) Prior Publication Data
US 2013/0091938 A1  Apr. 18, 2013

(51) Int. Cl.
*G01N 5/02* (2006.01)

(52) U.S. Cl.
USPC ...... 73/73; 73/74; 73/76; 73/865.3; 73/865.6; 405/52

(58) Field of Classification Search
USPC .............. 73/73, 74, 76, 865.3, 865.6; 405/52
See application file for complete search history.

(56) References Cited

U.S. PATENT DOCUMENTS

| | | | |
|---|---|---|---|
| 3,667,608 A * | 6/1972 | Burroughs et al. | 210/242.4 |
| 6,146,529 A * | 11/2000 | McCrory | 210/242.4 |
| 2011/0306491 A1* | 12/2011 | Belisle | 502/402 |
| 2011/0309031 A1* | 12/2011 | Hawthorne | 210/747.5 |
| 2012/0003045 A1* | 1/2012 | Singleton | 405/63 |
| 2012/0125854 A1* | 5/2012 | Holtslander | 210/660 |
| 2013/0168324 A1* | 7/2013 | Takamura et al. | 210/708 |

* cited by examiner

*Primary Examiner* — Hezron E Williams
*Assistant Examiner* — Hoang Nguyen
(74) *Attorney, Agent, or Firm* — Sughrue Mion, PLLC

(57) ABSTRACT

Traditional porous material testing does not provide a measure of how well the porous material will perform in oil spill conditions. We disclose a new system that can analyze and determine the absorptive capability and oil-selectivity of a porous material in a moving mixture of oil and water, under different environmental conditions of pressure and wind. Our system allows the porous material under test and the mixture of oil and water to experience complex motion trajectories, and we measure the absorption capacity as well as the rate of oil absorption under different environmental conditions.

8 Claims, 3 Drawing Sheets

SYSTEM TO MEASURE THE ABSORPTIVE CAPABILITIES OF POROUS MATERIALS USED IN OIL SPILL REMEDIATION

BACKGROUND

1. Technical Field

This invention relates to oil spill remediation and cleanup techniques where porous materials with oil-absorbing capabilities can be widely utilized.

2. Description of the Related Art

From Exxon-Valdez in 1989 to the more recent Deepwater Horizon in 2010, oil spills rank among the worst human-induced disasters our earth can face both environmentally and economically. The onset of these spills is extremely difficult, if not impossible, to predict in advance, and thus preventative measures are tough to institute. The next best thing is to minimize the lasting effects of oil spills by using effective remediation methods.

Right now, there are five major oil spill remediation methods that are in wide use: bioremediation, containment, dispersion, in situ burning, and skimming [1, 2, 3, 4].

Bioremediation involves using bacteria as well as other microorganisms that consume oil as part of their daily life to clean up the oil spill. Bacteria are living organisms, and they can perish due to unfavorable environmental conditions (bad weather, for example). Furthermore, bacteria remove oil extremely slowly. In many cases, the process of oil removal is too slow for bioremediation to be an effective cleanup technique.

Containment methods use large rubber booms to encircle the oil spill. The booms prevent further spreading of the oil, at least in the short-term. However, with time, the oil begins to form channels underneath and through crevices in the booms, and the oil begins to spread beyond the booms. Note that the booms do not absorb any oil, they just redirect it.

Dispersion involves using ships, planes, or helicopters, to spray dispersants on top of the oil spill. Dispersants allow oil and water, two previously immiscible liquids, to mix. The dispersants break the oil up into smaller pools. Dispersants cause problems though because the oil is not really removed—it has simply been integrated with the environment underneath, just removed from the surface. After some time, the oil integrated into the water harms the local ecosystems, and affects the economies that depend on the welfare of those aquatic ecosystems such as the fishing industry. Also, the dispersants are man-made chemicals that can be harmful to the aquatic ecosystems.

In situ burning involves using containment booms to separate a small pool of oil from the general sheet of oil spill, and then lighting the small pool of oil on fire. It is extremely effective at removing oil. However, by burning isolated slicks of oil, we may be solving one environmental problem, but we are drastically aggravating the another problem, namely global warming [6,7,8].

Skimming involves attaching machinery to boats and other ocean vessels that can, as the name of the practice suggests, skim oil right off of the surface of the water. The problem with skimming is that the technology only functions optimally in calm weather—if the water is turbulent and the environment windy, which in fact is extremely characteristic of the Gulf area in which the Deepwater Horizon oil spill took place, the surface is not necessarily just oil because the turbulence serves to "break" the sheet of oil on the top, and then the skimmer will then be skimming and filtering a mixture of oil and water.

Clearly, due to the limitations of current methods available for oil spill remediation, there is a massive effort to discover new and different methods [4, 5, 6, 7, 8]. Of late, researchers across the world have started focusing on a new method of oil spill remediation: the use of oil-absorbing porous materials. For example, a group of researchers in China have recently developed oleophilic carbon nanotube fibers that are capable of absorbing inordinate amounts of oil [7]. However, as with any new and aspiring technology, there are no systems available for measuring the efficacy of these porous materials in oil spill cleanup.

Note that most porous materials in the industry, including sol-gels, were not designed for use in oil spill remediation. The most common test of the absorbance of a porous material is to simply introduce the porous material into a given mixture of water and oil, and then allow the material to remain stagnant for a set period of time while it absorbs the oil. Such a measurement strategy is fine for common applications of porous materials, like paper towels.

However, a test where the porous material and the mixture are both stationary is not useful to identify porous materials that can be effective in oil-spill cleanups. We observed that the oil-absorbing capability (amount of absorption as well as the rate or absorption) of new porous materials like sol-gels depends on several factors like the type of motion the oil and water mixture is being subjected to by the environment, the wind patterns and air pressure, and the relative motion of the porous material and the mixture of oil and water.

SUMMARY

As our invention, we propose a new system to measure the oil-absorbing capability of porous materials by taking into account the type of motion the oil and water mixture is being subjected to by the environment, the prevailing wind patterns and air pressure, and the relative motion of the porous material with respect to the mixture of oil and water.

Low-cost systems that can quickly test the oil-absorbing capability of porous materials by taking into account the environmental conditions around the oil spill have not been developed. If such a system were available, then it would make it easy to quickly identify the appropriate porous material that is most efficient to clean up oil spills in different environmental conditions (oceans, rivers, lakes or other water bodies etc.).

Our invention exploits the physics behind relative motion. As an example, consider a simple scenario of an oil spill in the ocean. Assuming there are no high winds or adverse atmospheric conditions, the porous materials used for oil absorption would be stationary, while the water/and oil mixture would be in constant motion. However, if we assume the environment to be stationary, and we move the porous material, we can create the same relative motion between the porous material and the water-oil mixture. The two scenarios are physically indistinguishable. More complex relative motions between the porous material and the water-oil mixture can be created by independently considering simple motion vectors of the porous material and the mixture.

There are several advantages that accrue by the use of our proposed system: (a) Our system can be used to determine a quantitative measure of not only the absorbing capacity of a porous material, but we can also determine the rate of oil absorption under a variety of environmental conditions. (b) Our system can be used to rapidly identify the preferred porous material for a given oil-spill, based on the specific environmental conditions around the oil spill area, and (c)

Our system can accelerate the process of designing new porous materials that are specifically intended for use in oil spill scenarios.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein.

DETAILED DESCRIPTION OF PREFERRED EMBODIMENTS

Figure 1:
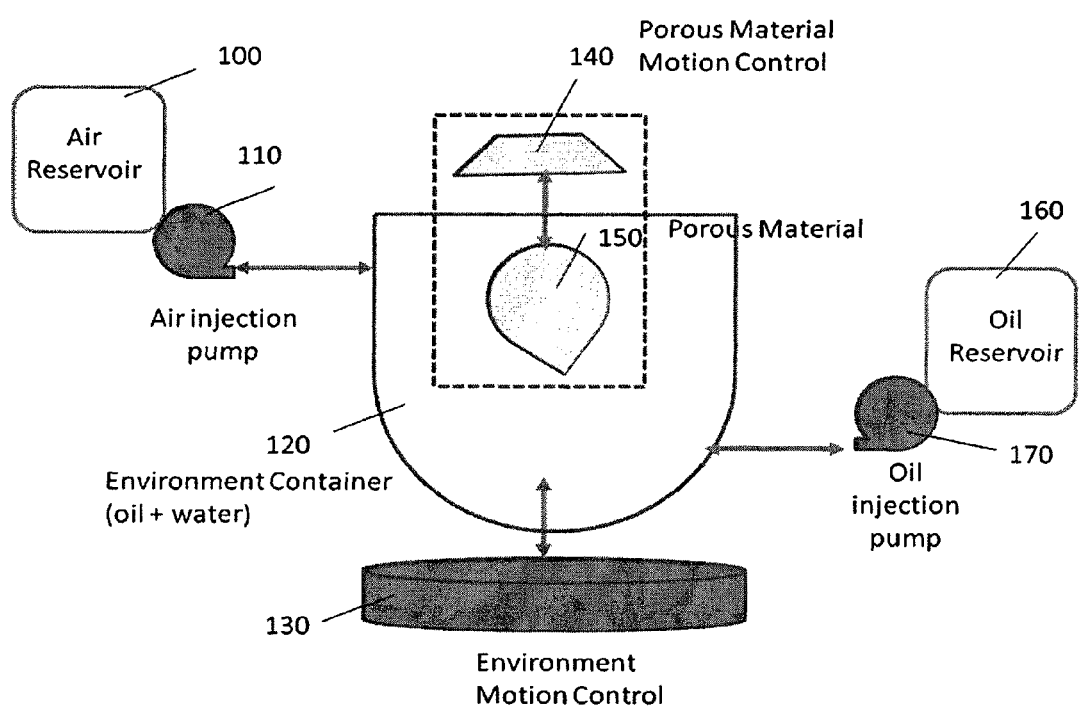
FIG. 1 shows the overall block diagram of a system for measuring the oil-absorbing capabilities of new porous materials like sol-gels in realistic environmental conditions.

FIG. 1 shows the block diagram of the proposed testing system. The full system has five subsystems: blocks 100 and 110 make up the wind injection system, blocks 120 and 130 make up the environmental motion control system, blocks 140 and 150 make up the porous material motion system, and blocks 160 and 170 make up the oil injection system. The fifth sub-system called the environment container 120 contains the mixture of water and oil. The oil injection system and the air injection system directly funnel into the environment container. A separate motion control system 130 is used to create movement of the mixture in the environment container. The porous material moves inside the environment container. Depending on the motion vectors of the porous material and the mixture in the environment container, the porous material may be fully or partially submerged in the oil and water mixture.

We describe a typical use case scenario of the proposed testing system. The testing process starts with a pre-determined quantity of water and oil mixture in the environment container. We attach the porous material under test to the porous material motion control assembly. The air injection system is used to create air flow in the environment container, and to maintain a specific pressure in the environment container. Depending on the motion vector chosen for the porous material, the porous material will follow a trajectory inside the mixture in the environment container. To create complex motion patterns, we also create specific motion patterns for the mixture in the environment container. The relative motion between the porous material and the mixture in the environment container determines the absorption capacity as well as the rate of oil absorption by the porous material under test, for a given density of oil in the mixture. The oil injection system can be used to adjust the concentration of oil in the environment container. For some porous materials, the rate of absorption of oil is also dependent on the density of oil in the mixture. We maintain the motion of the porous material and the mixture for a pre-set time. Then, we determine the weight of the porous material. The increase in weight of the porous material is an indicator of how much oil was absorbed by the porous material under the given environmental conditions in the environment container. The rate of absorption is calculated as the amount of oil absorbed per unit of time.

Figure 2:
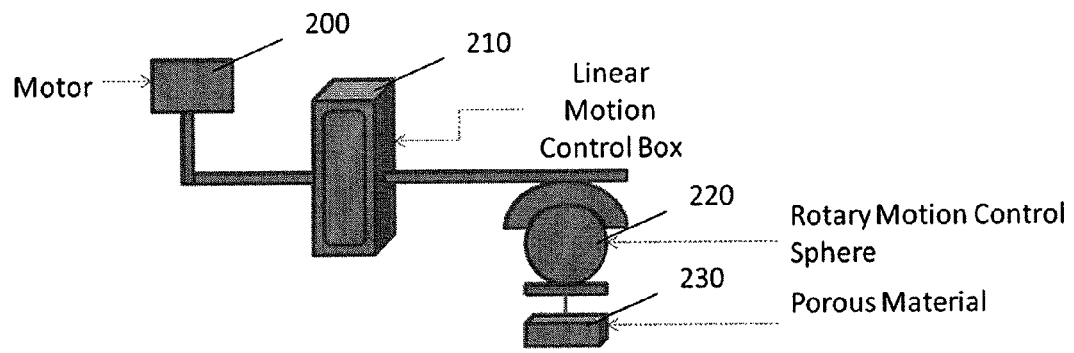
FIG. 2 shows the preferred embodiment of the motion control mechanism that allows the porous material to traverse different motion vectors.

FIG. 2 is an example of the porous material motion subsystem. At the heart of the controlled motion is the motor 200. The type of motor used does not affect the overall effectiveness or function of the system. A preferred embodiment of such a motor is a stepper motor that uses gears and electromagnets internally to create the rotary motion. The motor must generate enough power to create motion trajectories for the porous material 230. The linear motion control box 210 generates linear motion in response to the rotary movement of the motor. In a preferred embodiment, the linear motion control box has linear actuators that convert rotary motion of the motor into linear motion of steel rods that are also part of the linear motion control box. A linear actuator allows a steel rod to exhibit linear motion. By using three separate linear actuators, we create motion in three distinct directions: the x, y and z directions. For example, one linear actuator can make the porous material travel along the width (x-direction) of the environment container, another actuator can enable travel along the length (y-direction) of the environment container, and a third actuator can enable a change in depth (z-direction, up and down motion) with respect to the environment container. Block 220 is a sphere within a small holder, which resembles a synovial ball-and-socket joint in the human body. The sphere 220 creates the rotary motions of yaw, pitch, and roll for the porous material 230. Overall, the linear motion of the steel rods in block 210, and the rotary motion due to block 220 together contribute to the creation of complex motion trajectories for the platform that has the porous material. This subsystem is sufficient for the porous material to experience a full range of desired motion trajectories.

Figure 3:
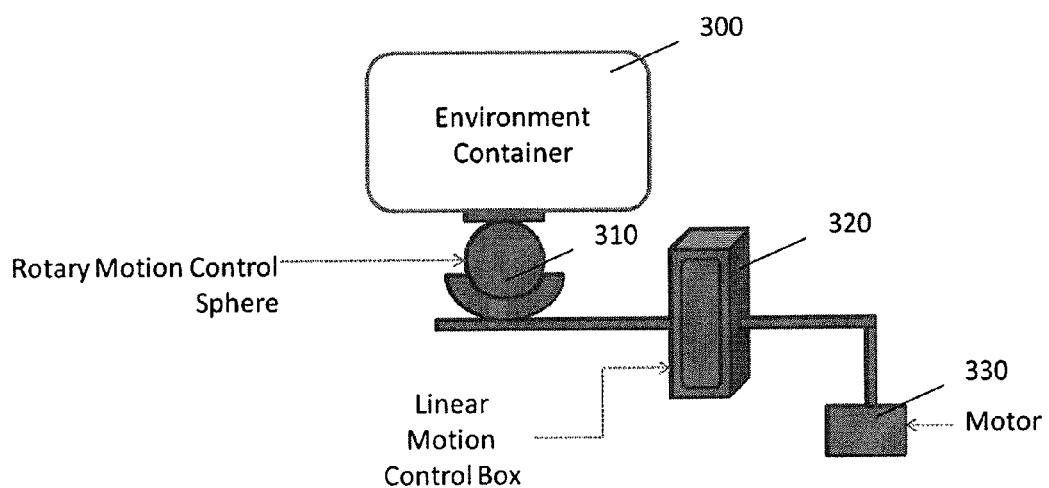
FIG. 3 shows the preferred embodiment of the motion control mechanism that allows the water and oil mixture to traverse different motion vectors.

FIG. 3 is an example configuration for the environmental motion control subsystem. Its design mirrors the principles that went into the design of the motion control system of FIG. 2. Block 330 is the motor, the power, behind the environmental motion control system. It is expected that the size of the environment container will generally be larger than the size of the porous material. Therefore, a more powerful motor might be in order for block 330 than block 200. Block 320 is the linear motion control box for the environmental system, which also has several linear actuators to move the environment container in any linear direction desired. Like the case of the porous motion control system, a ball and socket assembly is used to provide the rotary motion. By using a combination of linear motion in x, y or z directions, and rotary motion of pitch, yaw and roll, we are able to create complex motion trajectories for the mixture in the environment container. Special cases can also be constructed where, unlike the porous material motion control assembly, the environment container does not exhibit translation motion in x, y or z direction. The environment container only exhibits rotary motion around a pivot. Block 310 is the rotary sphere that is part of the ball and socket arrangement. The motion control subsystem for the environment container provides full range of rotary motion for the environment container, but no linear motion.

In real-life oil spill situations, the porous material in use and the environment will most likely have completely different paths of motions. For example, an open-ocean spill might have an environment exhibiting sinusoidal motion, the common trajectory associated with waves and tides, while the porous material might be making a sweeping motion while attached to the side of a boat, clearly not conforming to a sinusoidal motion.

Figure 4:
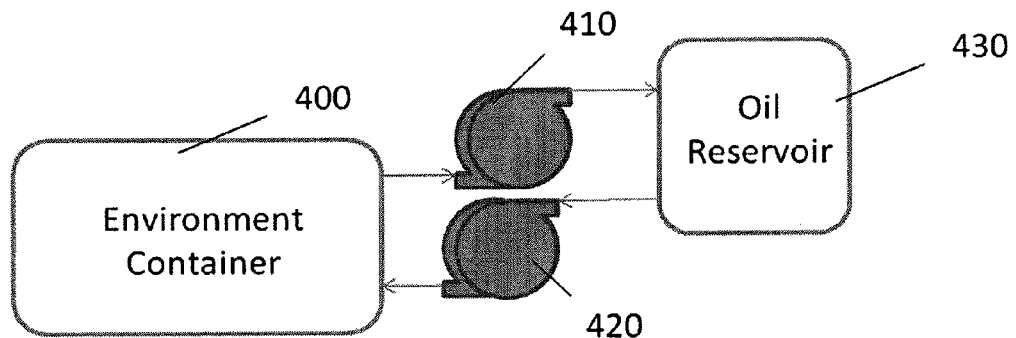
FIG. 4 shows a preferred embodiment of the oil injection system

FIG. 4 is an example of the oil injection system. This injection subsystem contains an oil reservoir, and two pumps, blocks 410 and 420. One of the pumps 420 helps transfer oil from the oil reservoir 430 into the environment container 400. The other pump 410 helps skim the oil on the surface in the water-oil mixture in the environment container 400, and transfer back into the oil reservoir 430. Together, these two pumps allow easy control of the density of oil, and the rate of injection of oil into the environment container. The reason for a dual-pump scenario is as follows. In real oil spills, the concentration of oil keeps changing. One example of inherent environment change is when multiple remediation methods are simultaneously put into place. Each will change the amount of oil in the environment independent of the effect of other remediation methods. Even if porous materials are utilized, they would operate in conjunction with other cleanup tactics such as skimmers. If both porous materials and skimmers are used, there will be oil removed from the environment by skimmers that is obviously not as a result of the porous material. The fact that the total oil is being removed at a faster rate than the porous material alone can remove it, affects the absorptive ability of the porous material. Our dual-pump configuration accurately simulates the effects that other remediation methods can have on the porous material's oil-absorbing capability.

A preferred embodiment can use an internal gear pump for blocks 410 or 420. The internal gear pump is ideal because it's easy to maintain, flexible in design, and incredibly simple, having only two moving parts. The dual-pump design is especially useful to simulate cases where more oil is still accumulating on the surface, because the source of the leak may not be patched up yet. In Deepwater Horizon, cleanup efforts began in less than a week, but it took 87 days to stop the oil from actually leaking from the ocean floor. The continuous addition of oil to the environment alters the oil to water ratio in the mixture, and it dramatically affects the absorbing capabilities of the porous material. With a dual-pump design, we can fill block 430 with oil, and pump it through to the bottom of the environment container at a user controlled rate, simulating an oil well that is still leaking in the midst of cleanup efforts.

Figure 5:
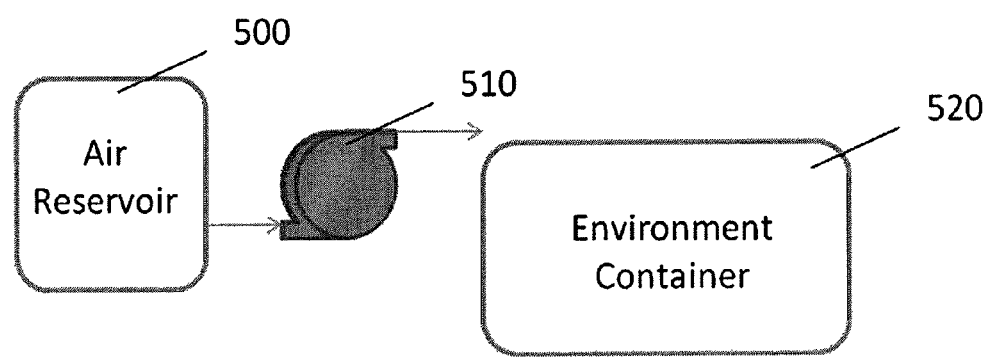
FIG. 5 shows a preferred embodiment of the air injection system

FIG. 5 is an example of a preferred embodiment of the wind injection subsystem. It consists of a compressed air reservoir 500. Typically, the reservoir is made of a material that can withstand pressure, like reinforced steel. The compressed air helps create wind effects. The wind injection system also has a pump, again, preferably an internal gear pump. This pump has a nozzle to direct compressed air into the environment container 520. The direction of the nozzle is adjustable so that air can be directed to different regions of the environment container. The nozzle is positioned just below the rim of the environment container.

Having described preferred embodiments of a system and method for measuring the oil-absorbing characteristics of a porous material (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A system for measuring the oil-absorbing capability of porous materials comprising of:
   (a) a container to hold mixture of oil and water,
   (b) an oil reservoir to hold oil,
   (c) an air reservoir to hold compressed air,
   (d) an oil injection system that includes the oil reservoir and controls for addition and removal of oil from the container, as well as a control to alter the rate of addition and removal of oil from the container,
   (e) an air injection system that includes the air reservoir, and controls for addition and removal of air into the container, as well as a control to alter the rate of addition and removal of air from the container,
   (f) a container motion control system that creates complex motion trajectories for the mixture in the container while ensuring that the porous material is fully, or partially submerged in the oil and water mixture in the container, and
   (g) a porous material motion control system that creates complex motion trajectories for the porous material under test so that the porous material is at all times within the container.

2. The system of claim 1, wherein the oil injection system includes a pump to inject oil into the base of the container, and a pump to skim oil from the top of the container.

3. The system of claim 1, wherein the porous material motion control includes linear actuators to provide three axes of linear motion in the x, y and z-direction for positioning the porous material in the oil and water mixture in the container.

4. The system of claim 1, wherein the porous material motion control includes a ball and socket assembly to provide rotary motion to the porous material.

5. The system of claim 1, wherein the container motion control system includes linear actuators to provide three axes of linear motion in the x, y and z directions for creating complex motion trajectories for the mixture in the container.

6. The system of claim 1, wherein the container motion control includes a ball and socket assembly to provide rotary motion to the mixture in the container.

7. The system of claim 1, where in the container motion control system only has the rotary motion provided by a ball and socket assembly, but it has no linear motion in the x, y, or z direction.

8. The system of claim 1, wherein the porous material motion control system only has the rotary motion provided by a ball and socket assembly, but it has no linear motion in the x, y or z direction.

* * * * *